United States Patent [19]
Zakoshansky et al.

[11] Patent Number: 6,066,767
[45] Date of Patent: May 23, 2000

[54] METHOD OF PURIFYING CUMENE HYDROPEROXIDE DECOMPOSITION PRODUCTS FROM HYDROXYACETONE AND FROM OTHER CARBONYLS

[75] Inventors: Vladimir Mikhailovitch Zakoshansky, Mt. Vernon, Ind.; Irina Ivanovna Vassilieva, St. Petersburg, Russian Federation

[73] Assignee: ILLA International, LLC, Reno, Nev.

[21] Appl. No.: 09/247,388

[22] Filed: Feb. 10, 1999

[51] Int. Cl.⁷ .......................... C07C 37/68; C07C 37/08; C07C 45/00
[52] U.S. Cl. .......................... 568/749; 568/750; 568/754; 568/758; 568/759; 568/798; 568/385
[58] Field of Search ..................... 568/749, 758, 568/750, 754, 759, 798, 385

[56] References Cited

U.S. PATENT DOCUMENTS 4,973,766  11/1990  Penzo et al. ............................ 568/754
5,491,268   2/1996  Cipullo .................................... 568/758

*Primary Examiner*—Paul J. Killos
*Assistant Examiner*—J. Parsa
*Attorney, Agent, or Firm*—Edward Etkin, Esq.

[57] ABSTRACT

Purification of cumene hydroperoxide cleavage products from hydroxyacetone and carbonyl compounds is accomplished via extraction of hydroxyacetone and carbonyl compounds from cleavage products with a circulating water-salt solution in an extractor during an extraction stage and subsequent conversion of hydroxyacetone and other carbonyl compounds into deep condensation products in a HAC reactor operating as a plug-flow reactor or mixing reactor or as their combination. The conversion/condensation process is conducted in the water-salt solution by treating the hydroxyacetone and carbonyl compounds with alkaline agents. Various homogenous and/or heterogeneous alkaline catalysts may be used. Optionally multiple sequential extraction stages may be connected to the HAC reactor for improved performance.

33 Claims, 3 Drawing Sheets

Master Table of Data for Example 1-10

| Example # | Content of HA and aldehydes In cleavage product | | Cumene, wt. % | Extraction condition | | | | | Content of HA&aldehydes in neutralized cleavage product, ppm | | Product acetone stability to oxidation | | Content of impurities in product phenol after IER treatment (after zeolite treatment), ppm | | | | |
|---|---|---|---|---|---|---|---|---|---|---|---|---|---|---|---|---|---|
| | HA, ppm | Aldehydes, ppm | | No. of stage | Temp. in reactor, °C | Residence time, min | [NaOH], wt. % | | HA | Aldehydes | Weight ratio Acetone/NaOH | Stability, hr | HA | MO | 2-MBF | Total carbonyls |
| Example 1 | 1300-2000 | 200-300 | 2-40 | - | - | - | - | | 1400-2100 | 250-500 | 1:0.004÷0.006 | 4÷8 | None | 0÷15 (0÷5) | 3÷70 (100÷200) | 50÷70 (20÷45) |
| Example 2 | 2000 | 300 | 12 | 1 | 80 | 60 | 1 | | 800 | 200 | 1:0.004 | 8÷10 | None | 0÷15 (0÷5) | 3÷15 (5÷30) | 45÷65 (15÷40) |
| Example 3 | 2000 | 300 | 40 | 1 | 80 | 60 | 1 | | 700 | 180 | 1:0.004 | 8÷10 | None | 0÷15 (0÷5) | 3÷12 (5÷25) | 45÷65 (15÷40) |
| Example 4 | 1300 | 200 | 12 | 1 | 80 | 60 | 1 | | 600 | 150 | 1:0.003 | 10 | None | 0÷15 (0÷5) | 3÷10 (5÷20) | 40÷50 (15÷30) |
| Example 5 | 2000 | 300 | 12 | 2 | 80 | 60 | 1 | | 180 | 60 | 1:0.002 | 12 | None | 0÷7 (0÷3) | 0÷3 (5÷10) | 40÷50 (15÷30) |
| Example 6 | 1300 | 200 | 12 | 2 | 80 | 120 | 0.5 | | 120 | 50 | 1:0.002 | 15 | None | 0÷10 (0÷3) | 0÷5 (5÷10) | 40÷50 (15÷30) |
| Example 7 | 2000 | 300 | 12 | 1 | 80 | 30 | 1 | | 800 | 200 | 1:0.004 | 8÷10 | None | 0÷15 (0÷5) | 3÷15 (5÷30) | 45÷65 (15÷40) |
| Example 8 | 2000 | 300 | 12 | 1 | 130 | 60 | 1 | | 800 | 200 | 1:0.004 | 8÷10 | None | 0÷10 (0÷5) | 3÷15 (5÷30) | 45÷65 (15÷40) |
| Example 9 | 2000 | 300 | 12 | 1 | 80 | 60 | - | | 820 | 210 | 1:0.004 | 8÷10 | None | 0÷15 (0÷5) | 3÷15 (5÷30) | 45÷65 (15÷40) |
| Example 10 | 2000 | 300 | 12 | 1 | 80 | 60 | - | | 700 | 190 | 1:0.004 | 8÷10 | None | 0÷15 (0÷5) | 3÷15 (5÷30) | 45÷65 (15÷40) |

Figure 3

METHOD OF PURIFYING CUMENE HYDROPEROXIDE DECOMPOSITION PRODUCTS FROM HYDROXYACETONE AND FROM OTHER CARBONYLS

BACKGROUND OF THE INVENTION

This invention relates to the field of decomposition product purification, and in particular, to a method of purifying cumene hydroperoxide decomposition products from hydroxyacetone and from other carbonyl impurities.

It is well known that in a typical cumene-based process of acetone and phenol production, a number of impurities are formed along with the main product and the various byproducts. These impurities significantly complicate the stage of product distillation and furthermore have a substantial negative effect on the quality of desired final products. Hydroxyacetone (hereinafter "HA") and various carbonyl compounds such as aldehydes, are most prominent among such impurities. The presence of HA causes the formation of 2-methylbenzofurane (hereinafter "2MBF") and consequently results in worsening of the quality of the product phenol. Furthermore, aldehydes that are present in product acetone reduce acetone's stability to oxidation, further lowering the quality of the final product.

Despite the substantial difference in existing schemes of cleavage product distillation, most commonly some form of a technique that involves separate treatment of acetone and phenol streams with main and acidic reagents, is applied to obtain final acetone and phenol products of desired quality and purity.

Typically, treatment of crude acetone or acetone streams is implemented by adding an aqueous caustic solution which converts the aldehydes into deep condensation products having high boiling temperature. These high condensation products are not distilled along with product acetone, and thus it is possible to obtain product acetone with a desired stability to oxidation.

The main difficulty in converting aldehydes into condensation products via addition of a caustic solution to the acetone stream (or to the product acetone distillation columns), is the extremely low solubility of non-organic compounds (such as NaOH) that are catalysts of aldehyde conversion reactions to deep condensation products, in organic compounds such as acetone.

In order to achieve a high degree of acetone purity from aldehydes, a significant quantity of a caustic catalyst (such as NaOH) must be added during the process. This results in clogging and deterioration of distribution devices of columns and heat-exchanging equipment used in the process. An even more serious disadvantage of the existing method of purification, is that the desired product acetone undergoes a condensation reaction to form mesityl oxide (hereinafter "MO") and diacetone alcohol (hereinafter "DAA"). The condensation reaction is highly undesirable for two reasons. First, the reaction results in loss of desired product, and second, the reaction complicates the treatment procedure of acetone because the amount of MO and DM in product acetone is limited.

Thus, the must commonly applied method for acetone purification solves the problem of aldehydes removal but at the same time creates new problems—damage to process equipment caused by a caustic agent and required removal of undesired products formed as a result of treatment of acetone with the alkaline catalyst.

Purification of crude phenol or phenol stream is typically carried out by alkaline or acidic agents such as aqueous caustic solutions, amines or with an acidic catalytic treatment based on ion-exchange resins or zeolites. Aldehydes, hydroxyacetone and mesityl oxide are converted into deep condensation products under the effect of alkaline or acidic catalysts. The boiling temperature of these condensation products is higher than phenol. As a result, it is possible to separate the condensation products from phenol via distillation to obtain product phenol of required quality.

The most commonly used method of purifying crude phenol is via an acidic catalytic treatment which is usually accomplished with the use of various types of ion-exchange resins with high acidity. As a result, aldehydes, MO and other impurities present in phenol are converted into deep condensation products and then separated from phenol via distillation.

HA present in crude phenol reacts with phenol to form 2MBF which is nearly impossible to separate from phenol by distillation at a product phenol column. Furthermore, phenol customers typically demand that the amount of 2MBF in product phenol should not exceed 15 ppm. The amount of 2MBF formed with ion-exchange resins is determined first by the level of HA concentration in crude phenol delivered to ion-exchange resin treatment. At HA concentration >30 ppm none of the existing ion-exchange resins are able to separate microimpurities from phenol in sufficient quantities. Thus phenol is typically purified from MO, alpha-methylstyrene and other impurities at the expense of undesirably forming 2MBF in amounts above the allowable limit.

A similar situation arises while using acidic zeolites for phenol treatment, as disclosed in commonly assigned U.S. Pat. No. 5,502,259 of Zakoshansky et al. Even though zeolites are superior to ion-exchange resins with respect to several parameters (i.e. a 4–8 times higher catalyst life, a degree of carbonyl purification that is at least twice better), they still do not completely solve the problem of a higher that desirable amount of 2MBF.

It should be noted that the amount of HA in a phenol stream arriving for purification is determined first by the level of overloading of cleavage products distillation columns, as well as by the amount of HA formed at the stage of cumene hydroperoxide cleavage.

Additionally, even a small increase in feed-rate (as low as 5% relative) causes the increase in the amount of HA delivered to the stage of acidic-catalytic purification several times (from 20–30% relative to 300–500% relative). Some variations of temperature profile or reflux flow to distillation column of phenol stream from acetone stream results in the same situation—increase in HA content in phenol stream and, hence, increase in 2MBF formed at the stage of acidic-catalytic purification.

Other attempts to solve the above-described problems have met with little success. For example, the technique of treating the phenol stream with a caustic solution as taught in U.S. Pat. No. 3,335,070 causes phenol to undergo a chemical reaction with the caustic solution to form a substantial amount of sodium phenate along with the formation of deep condensation products. This results in significant process overload at the dephenolation stage (i.e. conversion of sodium phenate to phenol) and also results in a great increase in waste water output. In another example, the technique of U.S. Pat. No. 3,692,845 proposes treating the phenol stream with amines for improved purification. However, during treatment of the phenol stream with amines, the products of amine reactions, along with aldehydes, hydroxyacetone and mesityl oxide, are removed from the process along with production waste phenol tar and then burnt. When the amine containing tar is burnt, nitrogen oxides are formed and released into the atmosphere creating undesirable levels of toxic pollution.

Thus, all the of the above-described currently implemented methods of phenol and acetone purification have a number of serious disadvantages resulting in difficulties in obtaining products of required quality.

SUMMARY OF THE INVENTION

The object of the present invention is to eliminate the previously described disadvantages of previously known acetone and phenol purification techniques and to produce final product acetone and phenol of required quality even under conditions of significant overloading of distillation columns (i.e. at higher content of HA and aldehydes in phenol and acetone streams during actual production). It should be noted that, as is well known in the art, the terms "purification" and "treatment" may be used interchangeably with respect to a process of removing impurities and undesirable compounds from various product streams.

In brief summary, in accordance with the present invention, purification of cumene hydroperoxide cleavage products from hydroxyacetone and the major portion of aldehydes is preferably accomplished in accordance with the following:

1. The inventive purification process is preferably carried out in a water-salt solution, not in an organic solution as is done in all previously known commercial processes;
2. Furthermore, the purification process is carried out before distillation stage of cleavage products, in contrast to previously known processes where purification is carried out during the distillation stage. The purification is preferably carried out as follows:
    a) Extracting HA and carbonyl compounds (e.g. aldehydes) with a water-salt solution at the neutralization stage of an existing process by adding a caustic agent; and
    b) Treating extragent containing HA and carbonyl compounds (e.g. aldehydes) in a separate reactor unit at a predetermined temperature and for a predetermined contact time sufficient to convert HA and carbonyl compounds into deep condensation products. Such reactions typically occur under the influence of homogeneous or heterogeneous catalysts.

In a more detailed summary, in accordance with the present invention, the purification process is accomplished via a single or a multiple stage extraction of HA and carbonyl compounds from cleavage products with a circulating water-salt-caustic solution. Extraction is conducted in an extractor at a temperature ranging from about 15 to about 80° C. Weight ratio of cleavage products to water-salt solution at the primary and additional (if any) extraction stages is kept within range from about 1:0.1 to about 1:10.

HA and carbonyl compounds, as products of cumene hydroperoxide cleavage, enter, after a primary extraction stage from an organic solution to a water-salt solution (that contains salts such as $Na_2SO_4$, and/or $NH_4NaSO_4$ and alkaline agents such as NaOH and/or $NH_4OH$) and are then converted to deep condensation products by action of alkaline agents at a temperature ranging from approximately 15° C. to approximately 130° C. The process of HA and aldehydes conversion to condensation products is conducted in the water-salt solution for a period of time sufficient to achieve a desired level of conversion of HA and aldehydes into deep condensation products. The above-described conversion process is preferably carried out in at least one reactor that may be a mixing reactor and/or plug-flow reactor.

After the desired conversion level is achieved, the water-salt solution is recycled to the primary extraction stage and to any additional extraction stages after which, the deep condensation products of HA and carbonyl compounds enter the organic solution, and subsequently continue to a distillation stage where they are easily separated from phenol and acetone. A portion of the water-salt solution is removed from the reactor to a dephenolation stage and process waste waters.

As described above, additional extraction stages may be connected sequentially after the primary extraction stages and connected to the reactor to achieve a greater level of purification. In an alternate embodiment of the present invention, one or more of the additional extraction stages may be connected back directly to the primary extraction stage bypassing the reactor. In yet another embodiment of the present invention where additional extraction stages are utilized, the reactor is connected to one or more of the additional extraction stages instead of the primary extraction stage. At least a portion of the stream exiting additional extraction stages is then circulated directly to the primary extraction stage. Optionally, when one of the additional extraction stages is not connected to the reactor, it may serve as a stage for converting HA and carbonyl compounds to the cleavage products.

BRIEF DESCRIPTION OF THE DRAWINGS

In the drawings, wherein like reference characters denote corresponding or similar elements throughout the various figures:

FIG. 3 is a master table summarizing parameters and results of examples 1 through 10 representative of prior art example 1 and of examples 2–9 conducted utilizing various embodiments of the purification process of the present invention.

DESCRIPTION OF THE PREFERRED EMBODIMENTS

The present invention is intended to operate as part of a complete process for production of high quality acetone and phenol. Accordingly, certain well-known process stages, such as for example, cumene oxidation, cleavage of cumene hydroperoxide, neutralization, dephenolation and distillation that occur before and after the inventive process, are referred to below but not described in detail. Furthermore, it should be understood that in describing embodiments of the process of the present inventions, varying quantities of products, impurities and agents are used by way of illustrative examples only and are not intended to serve as limitations for the inventive process other than as recited in the appended claims. Moreover, the present invention is intended to work in conjunction with any process involving cleavage of cumene hydroperoxide (CHP).

Figure 1:
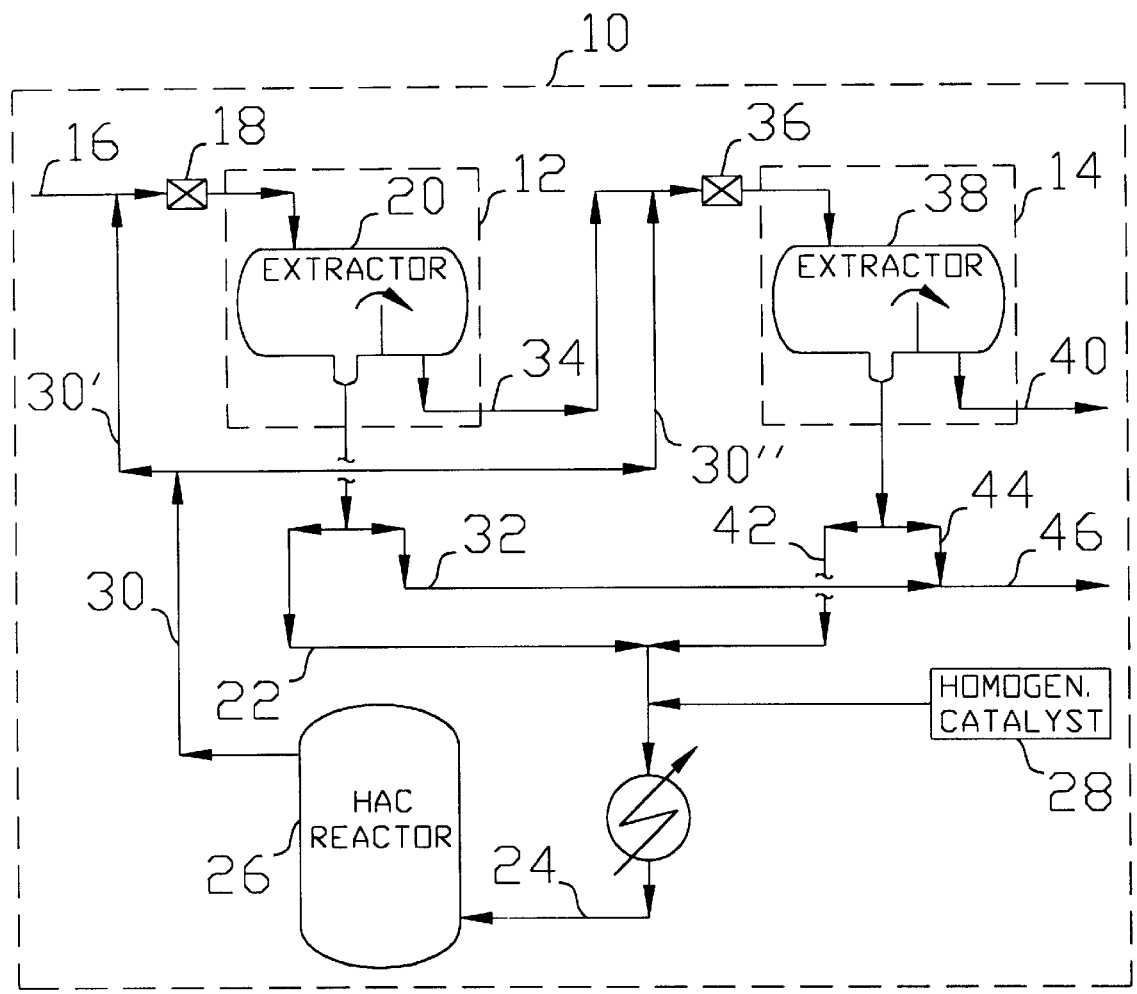
FIG. 1 schematically shows a first embodiment of the purification process of the present invention.

Referring now to FIG. 1, a simplified scheme of a preferred embodiment of an inventive process 10 is shown. While two extraction stages, a primary 12 extraction stage and additional extraction stage 14, are shown in FIG. 1, it should be understood that any number of sequential extraction stages, including, but not being limited to a single primary extraction stage, may be used as a matter of design choice without departing from the spirit of the present invention.

Cleavage products arrive to the process 10 via a stream 16. The cleavage products may contain 2 to 40 weight % of cumene, sulfuric acid which is a catalyst of a cumene hydroperoxide cleavage process, hydroxyacetone (hereinafter "HA") in the amount of 1300–2000 ppm and carbonyl compounds, such as for example, aldehydes (e.g. formaldehyde, acetic and propionic aldehyde), in the amount of 100–500 ppm. A stream 30', carrying a water-salt-caustic solution that serves as an extragent for HA and carbonyl compounds, joins stream 16 before stream 16 enters the primary extraction stage 12. Optionally, to improve mixing, the cleavage products and the water-salt-caustic solution are mixed in a mixer 18 prior to entry to the primary extraction stage 12; and similarly, a mixer 36 may also be employed prior to entry to the additional extraction stage 14. The primary extraction stage 12 is preferably conducted in an extractor 20 which may be any of the well known extractor types. Similarly, the additional extraction stage 14 may be conducted in an extractor 38. During each extraction stage 12 and 14, HA and carbonyl compounds are extracted from the cleavage products an the water-salt-caustic solution, in respective extractors 20 and 38.

The cleavage products in stream 16 may be neutralized to remove the sulphuric acid during the primary extraction stage 12 or, optionally, at a separate neutralization stage (not shown) prior to entering the primary extraction stage 12. The weight ratio of cleavage products to the water-salt-caustic solution is preferably kept within the range of about 1:0.1 to about 1:10, accordingly. Temperature at the primary extraction stage 12 is preferably maintained within the range of about 15 to about 80° C. Residence time at the primary extraction stage 12 is preferably from about 1 minute to about 30 minutes. As a result, conversion of HA and carbonyl compounds at the primary extraction stage 12 ranges from about 0.1 to about 40%.

After the specified residence time, the water-salt-caustic solution now containing HA and carbonyl compounds is directed to a HA and carbonyl (hereinafter "HAC") reactor 26 via first stream 22 which joins a similar stream 42, also containing water-salt-caustic solution with HA and carbonyl compounds, from the additional second extraction stage 14, and then via a stream 24. The HAC reactor 26 may be a mixing reactor, a plug flow reactor, or a combination of both reactor types. Optionally, reactor 26 may be implemented as a system of interconnected individual reactors. The HAC reactor 26 serves to enable conversion of HA and carbonyl compounds present in the water-salt-caustic solution to easily removable deep condensation products (without forming any 2MBF) with application of one or more alkaline agents.

Two general types of alkaline agents—homogenous and heterogeneous may be employed singly or together in accordance with the present invention, as a matter of design choice. Homogenous agents are soluble in a water-salt solution and thus may be added to steam 24, such as for example, via stream 28 prior to entry of stream 24 into the HAC reactor 26. Alternately, homogenous agents may be added to the stream 16, or to at least one of the extractors 20 and 38. Heterogeneous agents are insoluble and are typically embedded in the HAC reactor 26. Heterogeneous agents offer some superior characteristics over homogenous agents because they are present in the HAC reactor 26 at all times (and thus do not need to be delivered via a dedicated stream) and need to be replaced only infrequently.

Examples of homogenous catalysts that may be delivered via the stream 28 include, but are not limited to, bases such as NaOH, $NH_4OH$. Examples of heterogeneous catalysts that may be utilized and deployed in the HAC reactor 26 include, but are not limited to anion-exchange resins, zeolites, silcagel, aluminum oxides or alumosilicates with alkaline agents (such as NaOH, $NH_4OH$) being applied thereon, mixed oxides such as $SiO_2.Al_2O_3$, $SiO_2.MgO$ and oxides such as $SiO_2$, $Al_2O_3$, MgO.

Concentration of homogeneous catalyst in the water-salt solution in the HAC reactor 26 is preferably maintained at about 0.1 to about 20 weight %. The temperature in the HAC reactor 26 is preferably maintained within the range of about 15 to about 130° C. by heating and cooling the water-salt-caustic solution, as necessary, via one or more heat exchangers (not shown). The particular concentration value of the homogeneous catalysts, the particular temperature and residence time in the HAC reactor 26 while using both homogeneous and heterogeneous catalysts, are preferably selected so that conversion of HA exceeds 30% and conversion of carbonyl compounds is at least 50%.

After the appropriate HA and carbonyl compounds conversion goals are reached in the HAC reactor 26, the water-salt-caustic solution is recycled first via a stream 30 and then via the stream 30' to the primary extraction stage 12 and via a stream 30" to the additional extraction stage 14.

An organic solution from the primary extraction stage 12 containing 300–1000 ppm HA and 30–150 ppm carbonyl compounds is directed to the additional extraction stage 14 via a stream 34. It should be noted that a portion of homogenous catalysts present in the water-salt-caustic solution transfers to 20 cleavage products that get passed along via the stream 34 to the additional extraction stage 14.

A portion of the water-salt-caustic solution is removed from the primary extraction stage 12 via a stream 32, and from the additional extraction stage 14 via a stream 44, to stream 46 leading to a dephenolation (water-salt-caustic solution treatment from phenol) stage (not shown). After the additional extraction stage, the purified cleavage products are directed to a neutralization stage (not shown) via a stream 40 to neutralize any undesired salts and alkaline agents (such as NaOH and sodium phenate) with the use of neutralizing agent, such as $H_2SO_4$.

Figure 2:
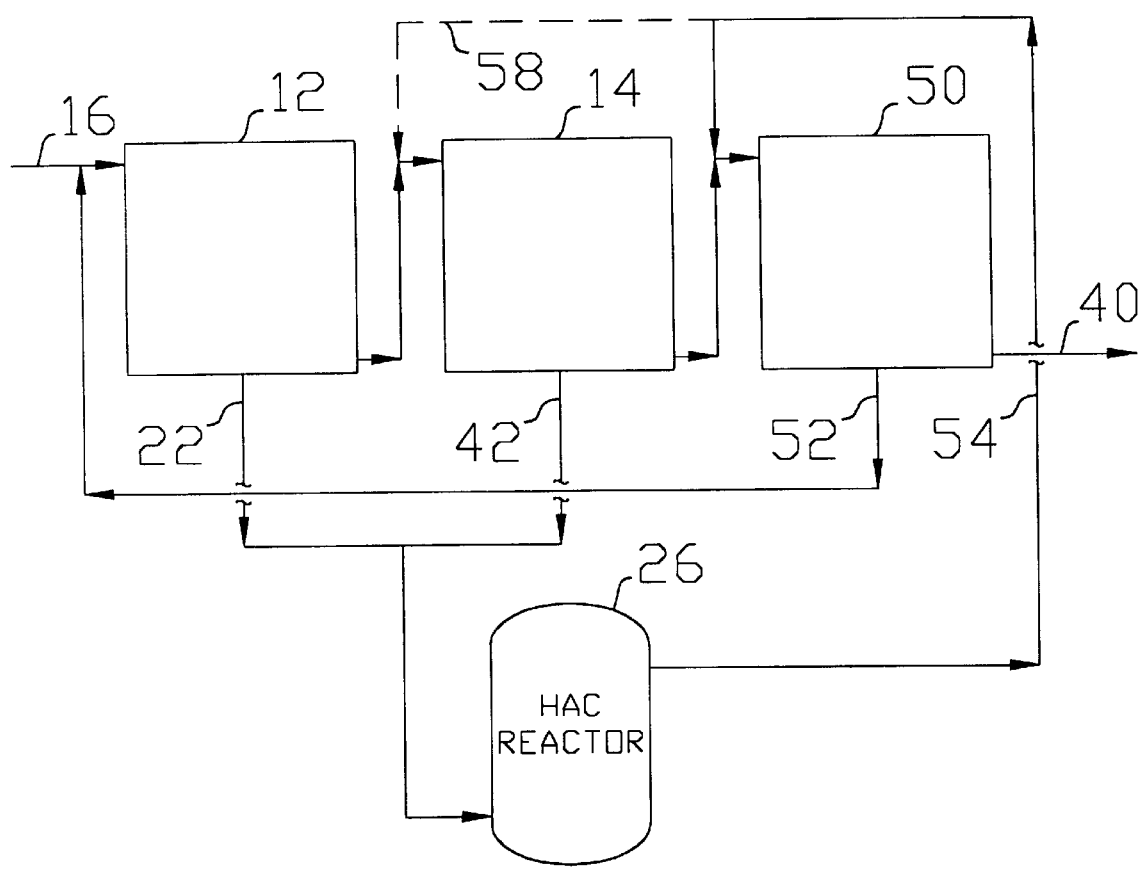
FIG. 2 schematically shows a second embodiment of the purification process of the present invention.

Referring now to FIG. 2, a second embodiment of the present invention is shown. When multiple extraction stages are utilized, it is possible to overload the HAC reactor 26. Thus, it may prove advantageous to recycle the water-salt-caustic solution from one or more additional stages directly back to the primary extraction stage 12, thus bypassing the HAC reactor 26. In FIG. 2, additional extraction stages 14 and 50 are shown. While streams 22 and 42 enter the HAC reactor 26, stream 52 from the last extraction stage 20 is recycled directly to the primary extraction stage 12. Optionally, if the capacity of the HAC reactor 26 is particularly small, stream 42 may also be directed to the primary extraction stage 12 bypassing the HAC reactor 26. The water-salt-caustic solution exiting HAC reactor 26 is directed to the additional extraction stages 14 and 50 via respective streams 58 and 54, instead of the primary extraction stage 12. At least a portion of the stream exiting the last additional extraction stage 50 is circulated directly to the primary extraction stage 12 in a "countercurrent" fashion. Optionally, stream 58 may be eliminated, thus delivering the water-salt-caustic solution to the last extraction stage 50 only. In this approach, the additional extraction stage 14 serves as a reactor for conversion of carbonyl compounds and HA to the cleavage products.

In summary the inventive and distinctive features of the process of the present invention include, but are not limited to, the following:

1. Treatment of cumene hydroperoxide cleavage products from HA and carbonyl compounds is accomplished before the distillation stage; and
2. Treatment of cumene hydroperoxide cleavage products from HA and carbonyl compounds is accomplished via extraction of HA and carbonyl compounds from the cleavage products with the water-salt solution and further conversion of HA and carbonyl compounds to deep condensation products via application of alkaline catalyst agents in the water-salt solution in the HAC reactor unit.
3. The combination of conversion, in dedicated reactors, of HA and carbonyl compounds both in the water-salt solution and in cleavage products, with the aid of alkaline catalysts.

The above-described advantages and distinctions of the present invention are illustrated by examples 2–10. Example 1 illustrates a prior art approach to cleavage products purification and is presented for comparative purposes only. Referring now to FIG. 3, examples 1÷10 are summarized therein in a Master Table. It should be noted that the below described examples are presented for illustrative purposes only and are not intended to limit the scope of the present invention.

EXAMPLE 1
(prior art)

Cleavage products containing 1300–2000 ppm of HA and 200–300 ppm of aldehydes are delivered to a neutralization stage where sulfuric acid (being a catalyst of cumene hydroperoxide cleavage stage) is neutralized. Cumene content in cleavage products is approximately 12 weight %. Neutralized cleavage products then arrive to a distillation stage. The content of HA and aldehydes at the neutralization stage slightly changes due to HA and aldehydes arriving along with recycle flows that are recycled to the neutralization stage from the distillation stage. Neutralized cleavage products containing 1400–2100 ppm HA and 250–500 ppm aldehydes are directed to distillation column where they are separated into acetone and phenol streams. The acetone stream, containing 500–1000 ppm aldehydes is sent to product acetone distillation columns. The acetone stream is treated with aqueous NaOH solution at weight ratio of acetone-NaOH (on a 100% NaOH basis) equal to 1: 0.004÷0.006. Parameter of product acetone stability to oxidation is 4÷8 hours.

The phenol stream is directed to a crude phenol column. Crude phenol containing such impurities as MO (5–100 ppm), HA (10–200 ppm), aldehydes (30–100 ppm), total carbonyls (300–500 ppm) and other impurities, is directed to acidic-catalytic treatment on ion-exchange resin (or zeolite). After being ion15 exchange (or zeolite) treated, a final product is produced at a product phenol column. The final product contains no HA, and has an MO content of 0–15 ppm (0–5 ppm), while content of total carbonyls is 50–70 ppm (20–45 ppm), and the content of 2MBF is 3–70 ppm (10–200 ppm).

EXAMPLE 2

Cleavage products containing 12 weight % cumene, 2000 ppm HA and 300 ppm carbonyl compounds arrive to the primary extraction stage where the cleavage products are neutralized and HA and aldehydes are extracted to a water-salt-caustic solution. The water-salt-caustic solution arrives to the primary extraction stage along with cleavage products. The content of NaOH in the water-salt solution is 1 weight %, the content of $Na_2SO_4$ is 18 weight %, the content of $NH_4OH$ is 0.01 weight %. The weight ratio of cleavage products to water-salt-caustic solution is kept as 1: 2.5. At the primary extraction stage:

a) Temperature is kept at 56° C.
b) Residence time is 20 minutes.
c) HA conversion is 20%.
d) Conversion of carbonyl compounds is 10%.

The water-salt-caustic solution, after being separated at the primary extraction stage, and containing NaOH at 0.65 weight %, $Na_2SO_4$ at 18 weight % and $NH_4OH$ at 0.005 weight %, is directed to the HAC reactor (operating in a plug-flow configuration) where HA and carbonyl compounds are converted to deep condensation products under the effect of alkaline agents. NaOH is added as the alkaline agent to the HAC reactor in an amount sufficient to maintain NaOH concentration at 1 weight %. Temperature in the HAC reactor is maintained at 80° C. Residence time in the HAC reactor is 60 minutes. HA conversion is 99% and carbonyl compound conversion is 50%.

After conversion of the HA and carbonyl compounds to condensation products, the water-salt-caustic solution is recycled to the primary extraction stage and is partly removed to a dephenolation stage (i.e. the stage of water-salt-caustic solution treatment from phenol). The organic solution from the primary extraction stage containing 700 ppm HA and 150 ppm carbonyl compounds is directed to a neutralization stage for neutralization of NaOH, $NH_4OH$ via $H_2SO_4$.

At the neutralization stage, the content of HA and carbonyl compounds in the cleavage products changes slightly due to HA and carbonyl compounds arriving along with recycle flows recycled to the neutralization stage from distillation. Neutralized cleavage products containing 800 ppm HA and 200 ppm carbonyl compounds are directed to a distillation column wherein they are separated into acetone and phenol streams. The acetone stream is treated with aqueous NaOH solution at weight ratio of acetone to NaOH (on a 100% basis) of 1: 0.004. The parameter of product acetone stability to oxidation is 10 hours.

The phenol stream is directed to a crude phenol column. Produced crude phenol containing such impurities as MO (5–50 ppm), HA (5–30 ppm), carbonyl aldehydes (10–30 ppm), total carbonyls (200–400 ppm) and other impurities, arrives to an acidic-catalytic treatment on ion-exchange resin (or zeolite). After being ion-exchange (or zeolite) treated, a final product is produced at the product phenol column. The final product contains no HA, MO content is 0–15 ppm (0–5 ppm if zeolite treated), content of total carbonyls is 45–65 ppm (15–40 ppm if zeolite treated), content of 2MBF is 3–15 ppm (5–30 ppm if zeolite treated).

EXAMPLE 3

The process is conducted as described in connection with example 2, other that the cleavage products contain 40 weight % cumene. The organic solution from the primary extraction stage containing 600 ppm HA and 120 ppm carbonyl compounds is directed to the neutralization stage. The acetone stream is treated with aqueous NaOH solution at a weight ratio of acetone to NaOH (on a 100% basis) of 1: 0.0035. The parameter of product acetone stability to oxidation is 10 hr.

Produced crude phenol, which contains such impurities as MO (5–50 ppm), HA (5–25 ppm), aldehydes (10–25 ppm), total carbonyls (200–350 ppm) and other impurities, arrives to the acidic-catalytic treatment on ion-exchange resin (or zeolite). After being ion-exchange (or zeolite) treated, the final product is produced at the product phenol column. The final product contains no HA, MO content is 0–15 ppm (0–5 ppm if zeolite treated), content of total carbonyls is 45–65 ppm (15–40 ppm if zeolite treated), content of 2MBF is 3–12 ppm (5–25 ppm if zeolite treated).

EXAMPLE 4

The process is conducted as described in connection with example 2, other that the cleavage products contain 1300 ppm of HA and 200 ppm aldehydes.

The organic solution from the primary extraction stage containing 500 ppm HA and 100 ppm carbonyl compounds is directed to the neutralization stage. The cleavage products enter the distillation stage containing 600 ppm HA and 150 ppm aldehydes. The acetone stream is treated with aqueous NaOH solution at weight ratio of acetone to NaOH (on a 100% basis) of 1: 0.003. The parameter of product acetone stability to oxidation is 10 hours. Produced crude phenol containing such impurities as MO (5–50 ppm), HA (5–20 ppm), aldehydes (10–20 ppm), total carbonyls (200–350 ppm) and other impurities arrives to the acidic-catalytic treatment on ion-exchange resin (or zeolite). After being ion-exchange (or zeolite) treated, the final product is produced at the product phenol column. The final product contains no HA, MO content is 0–15 ppm (0–5 ppm if zeolite treated), content of total carbonyls is 45–65 ppm (15–40 ppm if zeolite treated), content of 2MBF is 3–10 ppm (5–20 ppm if zeolite treated).

EXAMPLE 5

The process is conducted as described in connection with example 2, other that two additional extraction stages are implemented sequentially after the primary extraction stage. The water-salt solution from the last extraction stage is delivered directly to the primary extraction stage, bypassing the HAC reactor. The temperature in the HAC reactor is maintained at 60° C., while the NaOH concentration is maintained at 0.35 weight %. The organic solution from the additional extraction stage containing 100 ppm HA and 30 ppm aldehydes is directed to the neutralization stage. Neutralized cleavage products enter the distillation stage containing 110 ppm HA and 35 ppm aldehydes where acetone and phenol streams are separated.

The acetone stream containing 120 ppm aldehydes is sent to the product acetone columns. The acetone stream is treated with aqueous NaOH solution at a weight ratio of acetone to NaOH (on a 100% basis) of 1: 0.002. The parameter of product acetone stability to oxidation is 12 hours.

The phenol stream is sent to the crude phenol column. The produced crude phenol containing such impurities as MO (5–30 ppm), HA (5–10 ppm), aldehydes (10–20 ppm), total carbonyls (100–300 ppm) and other impurities arrives to the acidic-catalytic treatment on ion-exchange resin (or zeolite). After being ion-exchange (or zeolite) treated, the final product is produced at the product phenol column. The final product contains no HA, MO content is 0–7 ppm (0–3 ppm if zeolite treated), content of total carbonyls is 40–50 ppm (15–30 ppm if zeolite treated), content of 2MBF is 0–3 ppm (5–10 ppm if zeolite treated).

EXAMPLE 6

The process is conducted as described in connection with example 5, other that:

1) The water-salt solution is not delivered to the second extraction stage, while cleavage products from the primary extraction stage are delivered to the second extraction stage where conversion of HA and carbonyl compounds takes place in an organic solution, before continuing to the last extraction stage; and
2) The cleavage products contain 1300 ppm HA and 200 ppm aldehydes.

The temperature in the HAC reactor is maintained at 60° C., while the NaOH concentration is maintained at 0.25 weight % in the water-salt solution and at 0.15 weight % in the organic solution.

The organic solution from the last extraction stage containing 80 ppm HA and 25 ppm aldehydes is directed to the neutralization stage. Neutralized cleavage products enter the distillation stage containing 85 ppm HA and 25 ppm aldehydes, where acetone and phenol streams are separated.

The acetone stream containing 130 ppm aldehydes is sent to the product acetone columns. The acetone stream is treated with aqueous NaOH solution at a weight ratio of acetone to NaOH (on a 100% basis) of 1 : 0.024. The parameter of product acetone stability to oxidation is 15 hours.

The phenol stream is sent to the crude phenol column. The produced crude phenol containing such impurities as MO (5–30 ppm), HA (5–10 ppm), aldehydes (10–20 ppm), total carbonyls (100–300 ppm) and other impurities arrives to the acidic-catalytic treatment on ion-exchange resin (or zeolite). After being ion-exchange (or zeolite) treated, the final product is produced at the product phenol column. The final product contains no HA, MO content is 0–7 ppm (0–3 ppm if zeolite treated), content of total carbonyls is 25–40 ppm (10–20 ppm if zeolite treated), content of 2MBF is 0–5 ppm (5–10 ppm if zeolite treated).

EXAMPLE 7

The process is conducted as described in connection with example 2, other that the cleavage products contain 1–2 weight % cumene and the content of the caustic agent (NaOH) in water-salt-caustic solution is 0.5 weight %. To achieve HA conversion of 99% and aldehydes conversion of 50%, the residence time in the HAC reactor is 2 hours. Neutralized cleavage products contain 800 ppm HA and 200 ppm aldehydes. The characteristics of the product acetone and product phenol obtained are shown in FIG. 3.

EXAMPLE 8

The process is conducted as described in connection with example 2, other that the temperature in the HAC reactor is maintained at 130° C. Residence time in HAC reactor is 30 minutes which results in HA conversion of 97%, and aldehydes conversion of 40%. Neutralized cleavage products contain 800 ppm HA, 200 ppm aldehydes. The characteristics of the product acetone and product phenol obtained are shown in FIG. 3.

EXAMPLE 9

The process is conducted as described in connection with example 2, other that a heterogeneous catalyst anionite is used as a catalyst in the HAC reactor. A Diaion SA–10A is used as the anionite in this example. Residence time in the HAC reactor is maintained at 1 hr resulting in HA conversion of 95% and aldehydes conversion of 37%. Neutralized cleavage products contain 820 ppm HA and 210 ppm aldehydes. The characteristics of the product acetone and product phenol obtained are shown in FIG. 3.

EXAMPLE 10

The process is conducted as described in connection with example 2, other that a Y-type zeolite with NaOH applied thereon is used as a catalyst in the HAC reactor. Residence time in the HAC reactor is maintained at 1 hr, resulting in HA conversion of 96% and aldehydes conversion of 38%. Neutralized cleavage products contain 790 ppm HA and 190 ppm aldehydes. The characteristics of the product acetone and product phenol obtained are shown in FIG. 3.

Thus, while there have shown and described and pointed out fundamental novel features of the invention as applied to preferred embodiments thereof, it will be understood that various omissions and substitutions and changes in the form and details of the devices and methods illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

We claim:

1. A method for purifying cumene hydroperoxide cleavage products from hydroxyacetone and carbonyl compounds in a purification process system comprising a primary extraction stage conducted in an extractor, said method comprising the steps of:

a) applying, prior to said primary extraction stage, a water-salt solution to the cumene hydroperoxide cleavage products so that at said primary stage the hydroxyacetone and the carbonyl compounds are extracted from the cumene hydroperoxide cleavage products by action of the water-salt solution; and b) treating, after said primary extraction stage, said water-salt solution and the hydroxyacetone and carbonyl compounds, with an alkaline agent to form a water-salt-caustic solution and to convert the hydroxyacetone and carbonyl compounds into condensation products thereby purifying the cumene hydroperoxide cleavage products.

2. The method of claim 1, further comprising the step of (c) mixing said water-salt solution with the cumene hydroperoxide cleavage products in a mixer prior to said step (a).

3. The method of claim 1, wherein the cumene hydroperoxide cleavage products contain from about 2 to about 40 weight % cumene.

4. The method of claim 1, wherein said water-salt-caustic solution contains at least one of $Na_2SO_4$, $NH_4NaSO_4$, NaOH, $NH_4OH$, sodium phenate, acetone and phenol.

5. The method of claim 1, wherein said alkaline agent comprises at least one of: a heterogeneous catalyst and a homogenous catalyst.

6. The method of claim 5, wherein said heterogeneous catalyst comprises at least one of: anion-exchange resins, basic zeolites, zeolites, silicagel, aluminum oxides and alumosilicates, and wherein said homogenous catalyst comprises at least one of: NaOH, $NH_4OH$, at least one mixed oxide selected from $SiO_2.Al_2O_3$ and $SiO_2.MgO$, and at least one oxide selected from $SiO_2$, $Al_2O_3$, and MgO.

7. The method of claim 4, wherein said water-salt solution contains up to about 10 weight % phenol and up to about 10 weight % acetone.

8. The method of claim 4, wherein $Na_2SO_4$ concentration ranges from about 10 to about 20 weight %.

9. The method of claim 4, wherein NaOH concentration ranges from about 0.1 to about 20 weight %.

10. The method of claim 4, wherein $NH_4OH$ concentration is equal to or below about 1 weight %.

11. The method of claim 1, wherein said step b) comprises the steps of:

(d) delivering said water-salt solution along with hydroxyacetone and carbonyl compounds to an HAC reactor for treatment with said alkaline agent to form a water-salt-caustic solution therein; and (e) retaining said water-salt-caustic solution in said HAC reactor for a sufficient period of time to achieve condensation of the hydroxyacetone and the carbonyl compounds via said treatment with said alkaline agent, wherein said alkaline agent comprises at least one of: a heterogeneous catalyst and a homogenous catalyst.

12. The method of claim 11, wherein said HAC reactor comprises a predetermined quantity of said at least one heterogeneous catalyst disposed therein.

13. The method of claim 11, further comprising the step of:

(f) prior to said step (d), adding said at least one homogenous catalyst to said water-salt solution.

14. The method of claim 11 wherein said HAC reactor is at least one of: a mixing reactor and a plug-flow reactor.

15. The method of claim 11, further comprising the step of:

(g) after said step e), recycling said water-salt-caustic solution exiting said HAC reactor after said sufficient period of time, to said primary extraction stage, such that said water-salt-caustic solution enters said primary extraction stage along with the cumene hydroperoxide cleavage products.

16. The method of claim 15, further comprising the step of:

(h) maintaining a weight ratio of the cumene hydroperoxide cleavage products to said water-salt-caustic solution within a range of about 1:0.1 to about 1:10 at said primary extraction stage during said step (a).

17. The method of claim 1, wherein said step (a) at said primary extraction stage is conducted at a temperature of about 15 to about 80° C.

18. The method of claim 1, wherein said step (b) after said primary extraction stage is conducted at a temperature of about 15 to about 130° C.

19. The method of claim 1, further comprising at least one additional extraction stage connected sequentially to said primary extraction stage, each said at least one additional extraction stage being conducted in a corresponding additional extractor, further comprising the steps of:

(i) delivering a first portion of said water-salt-caustic solution and the hydroxyacetone and carbonyl compounds from a current extraction stage selected from said primary extraction stage and said at least one additional extraction stage, to a subsequent additional extraction stage; and (j) repeating said step (a) at each of said at least one additional extraction stage.

20. The method of claim 19, further comprising the steps of (k) delivering a second portion of said water-salt-caustic solution along with hydroxyacetone and carbonyl compounds from each of said at least one additional extraction stage to a common HAC reactor for treatment with said alkaline gent; and (l) retaining said water-salt-caustic solution in said common HAC reactor for a sufficient period of time to achieve condensation of the hydroxyacetone and the carbonyl compounds via said treatment with said alkaline agent, wherein said alkaline agent comprises at least one of: a heterogeneous catalyst and a homogenous catalyst.

21. The method of claim 20, further comprising the step of:
(m) after said step (l), recycling said water-salt-caustic solution exiting said common HAC reactor after said sufficient period of time, to at least one of:
1) said primary extraction stage, and
2) said at least one additional extraction stage.

22. The method of claim 20, further comprising the steps of:
n) after said step l), recycling said water-salt-caustic solution exiting said common HAC reactor after said sufficient period of time, to a last additional extraction stage of said at least one additional extraction stage; and
o) delivering said second portion of said water-salt-caustic solution from said last additional extraction stage to at least one of:
1) said primary extraction stage, and
2) said at least one additional extraction stage.

23. The method of claim 19, comprising the step of:
p) delivering a second portion of said water-salt-caustic solution along with hydroxyacetone and carbonyl compounds from at least one of said at least one additional extraction stage to said primary extraction stage such that said water-salt-caustic solution enters said primary extraction stage along with the cumene hydroperoxide cleavage products.

24. The method of claim 19, wherein concentration of said alkaline agent in said water-salt solution is the same at each of said at least one additional extraction stage.

25. The method of claim 19, wherein concentration of said alkaline gent in said water-salt solution is the different at each of said additional extraction stage.

26. The method of claim 1, wherein hydroxyacetone conversion at said primary extraction stage ranges from about 0.1 to about 40%.

27. The method of claim 1, wherein carbonyl compounds conversion at said primary extraction stage ranges from about 0.1 to about 40%.

28. The method of claim 11, wherein hydroxyacetone conversion in said HAC reactor is from about 30 to about 99%.

29. The method of claim 11, wherein conversion of carbonyl compounds in said HAC reactor is at least about 50%.

30. The method of claim 1, wherein the carbonyl compounds comprise aldehydes.

31. The method of claim 19, wherein said at least one additional extraction stage is conducted in a single multi-section extractor.

32. The method of claim 20, wherein said at least one additional extraction stage comprises a first additional extraction stage and a second additional extraction stage, further comprising the steps of:
(q) after said step (l), recycling said water-salt-caustic solution exiting said common HAC reactor after said sufficient period of time, to said second additional extraction stage;
(r) utilizing said first additional extraction stage to convert the carbonyl compounds and HA in an organic solution; and
s) delivering at least a portion of said water-salt-caustic solution form said second additional extraction stage to said primary extraction stage.

33. The method of claim 14, wherein said HAC reactor comprises a plurality of interconnected reactors.

* * * * *